United States Patent
Silvestrini et al.

(10) Patent No.: US 10,334,883 B2
(45) Date of Patent: Jul. 2, 2019

(54) CARTRIDGE FOR AN AEROSOL-GENERATING SYSTEM AND AN AEROSOL-GENERATING SYSTEM COMPRISING A CARTRIDGE

(71) Applicant: Philip Morris Products S.A., Neuchatel (CH)

(72) Inventors: Patrick Charles Silvestrini, Neuchatel (CH); Judith Waller, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/544,887

(22) PCT Filed: Dec. 21, 2016

(86) PCT No.: PCT/EP2016/082223
§ 371 (c)(1),
(2) Date: Jul. 20, 2017

(87) PCT Pub. No.: WO2017/108983
PCT Pub. Date: Jun. 29, 2017

(65) Prior Publication Data
US 2018/0271152 A1    Sep. 27, 2018

(30) Foreign Application Priority Data
Dec. 22, 2015  (EP) .................................... 15202201

(51) Int. Cl.
*A24F 47/00* (2006.01)
*A61M 15/00* (2006.01)
(Continued)

(52) U.S. Cl.
CPC .......... *A24F 47/008* (2013.01); *A24B 15/167* (2016.11); *A61M 15/0003* (2014.02); *A61M 15/06* (2013.01); *A61M 2205/3653* (2013.01)

(58) Field of Classification Search
CPC combination set(s) only.
See application file for complete search history.

(56) References Cited

U.S. PATENT DOCUMENTS

| 4,765,348 A | 8/1988 | Honeycutt |
| 7,234,464 B2 * | 6/2007 | Goede ............... A61M 15/0066 128/200.14 |

(Continued)

FOREIGN PATENT DOCUMENTS

| CN | 104634914 A | 5/2015 |
| CN | 104655778 A | 5/2015 |

(Continued)

OTHER PUBLICATIONS

Combined Chinese Office Action and Search Report dated Jan. 31, 2018 in Chines Patent Application No. 201680005069.0 (with English translation), citing documents AO and AP therein, 11 pages.

(Continued)

*Primary Examiner* — LaToya M Louis
(74) *Attorney, Agent, or Firm* — Oblon, McClelland, Maier & Neustadt, L.L.P.

(57) ABSTRACT

A cartridge for an aerosol-generating system is provided, including an elongate first compartment having a length $L_1$, a maximum transverse cross-sectional area $A_1$, a first air inlet, and a first air outlet, and containing a nicotine source including a first carrier material loaded with between about 1 mg and about 50 mg of nicotine; and an elongate second compartment having a length $L_2$, a maximum transverse cross-sectional area $A_2$, a second air inlet, and a second air outlet, and containing an acid source. The first and second compartments are arranged in parallel within the cartridge and the ratio $(L_1)^2:A_1$ is at least about 12:1 and the ratio $(L_2)^2:A_2$ is at least about 12:1. An aerosol-generating system is also provided, including the cartridge; an aerosol-gener- (Continued)

ating device including a housing defining a cavity to receive at least a portion of the cartridge; and a heater to heat the first and second compartments.

15 Claims, 3 Drawing Sheets

(51) Int. Cl.
  *A24B 15/16* (2006.01)
  *A61M 15/06* (2006.01)

(56) References Cited

U.S. PATENT DOCUMENTS

| | | | | |
|---|---|---|---|---|
| 2005/0263618 | A1* | 12/2005 | Spallek | A61M 15/0065 239/433 |
| 2005/0268908 | A1* | 12/2005 | Bonney | A61M 15/0045 128/203.15 |
| 2014/0060527 | A1* | 3/2014 | Liu | A61M 15/06 128/202.21 |
| 2014/0261487 | A1* | 9/2014 | Chapman | D04C 1/06 131/328 |
| 2014/0261488 | A1* | 9/2014 | Tucker | A24F 47/008 131/328 |
| 2016/0081395 | A1 | 3/2016 | Thorens et al. | |
| 2016/0089508 | A1* | 3/2016 | Smith | A61M 15/06 128/200.16 |
| 2016/0219938 | A1 | 8/2016 | Mamoun et al. | |

FOREIGN PATENT DOCUMENTS

| | | |
|---|---|---|
| JP | 2007-512880 A | 5/2007 |
| JP | 2012-520736 A | 9/2012 |
| JP | 2015-512262 A | 4/2015 |
| KR | 10-2016-0145838 A | 12/2016 |
| WO | WO 2005/053444 A1 | 6/2005 |
| WO | WO 2008/121610 A1 | 10/2008 |
| WO | WO 2014/187770 A2 | 11/2014 |
| WO | WO 2015/038981 A2 | 3/2015 |
| WO | WO 2015/177043 A1 | 11/2015 |
| WO | WO 2015/177254 A1 | 11/2015 |
| WO | WO 2015/197627 A1 | 12/2015 |
| WO | WO 2017/032695 A1 | 3/2017 |

OTHER PUBLICATIONS

International Search Report and Written Opinion dated Mar. 23, 2017 in PCT/EP2016/082223, filed Dec. 21, 2016.
Office Action dated Nov. 29, 2017 in Japanese Patent Application No. 2017-537390 (with English language translation) citing documents AO-AS therein, 9 pages.
Notice of Allowance dated Feb. 17, 2018 in Korean Patent Application No. 10-2017-7019014 (with English translation), citing document AO therein, 3 pages.

* cited by examiner

CARTRIDGE FOR AN AEROSOL-GENERATING SYSTEM AND AN AEROSOL-GENERATING SYSTEM COMPRISING A CARTRIDGE

The invention relates to a cartridge for use in an aerosol-generating system and an aerosol-generating system comprising such a cartridge. In particular, the invention relates to a cartridge assembly comprising a nicotine source and an acid source for use in an aerosol-generating system for the in situ generation of an aerosol comprising nicotine salt particles and an aerosol-generating system comprising such a cartridge.

Devices for delivering nicotine to a user comprising a nicotine source and a volatile delivery enhancing compound source are known. For example, WO 2008/121610 A1 discloses devices in which nicotine and an acid, such as pyruvic acid, are reacted with one another in the gas phase to form an aerosol of nicotine salt particles that is inhaled by the user.

Differences between the vapour concentrations of nicotine and the acid in such devices may disadvantageously lead to an unfavorable reaction stoichiometry or the delivery of excess reactant, such as unreacted nicotine vapour or unreacted acid vapour to a user. To control and balance the vapour concentrations of nicotine and acid to yield an efficient reaction stoichiometry, it has been proposed to heat the nicotine and acid in devices of the type disclosed in WO 2008/121610 A1.

It would be desirable to provide an aerosol-generating system comprising a nicotine source and an acid source for the in situ generation of an aerosol comprising nicotine salt particles that enables the nicotine source and the acid source to be heated uniformly. It would also be desirable to provide an aerosol-generating system comprising a nicotine source and an acid source for the in situ generation of an aerosol comprising nicotine salt particles that facilitates release of nicotine vapor from the nicotine source and acid vapour from the acid source. It would further be desirable to provide an aerosol-generating system comprising a nicotine source and an acid source for the in situ generation of an aerosol comprising nicotine salt particles that enables more constant aerosol generation throughout the different stages of use of the aerosol-generating system.

According to the invention there is provided a cartridge for use in an aerosol-generating system, the cartridge comprising: an elongate first compartment having a length $L_1$ and a maximum transverse cross-sectional area $A_1$, the first compartment having a first air inlet and a first air outlet and containing a nicotine source comprising a first carrier material loaded with between about 1 milligram and about 50 milligrams of nicotine; and an elongate second compartment having a length $L_2$ and a maximum transverse cross-sectional area $A_2$, the second compartment having a second air inlet and a second air outlet and containing an acid source, wherein the first compartment and the second compartment are arranged in parallel within the cartridge and wherein the ratio $(L_1)^2 : A_1$ is at least about 12:1 and wherein the ratio $(L_2)^2 : A_2$ is at least about 12:1.

According to the invention there is also provided an aerosol-generating system comprising: a cartridge according to the invention; and an aerosol-generating device comprising: a housing defining a cavity for receiving at least a portion of the cartridge; and a heater for heating the first compartment and the second compartment of the cartridge.

According to the invention there is further provided an aerosol-generating system comprising: a cartridge according to the invention comprising a heater configured to heat the first compartment and the second compartment; and an aerosol-generating device comprising: a housing defining a cavity for receiving at least a portion of the cartridge; and a power supply configured to supply power to the heater of the cartridge.

Advantageously, providing an elongate first compartment having a length $L_1$ and a maximum transverse cross-sectional area $A_1$ and an elongate second compartment having a length $L_2$ and a maximum transverse cross-sectional area $A_2$, wherein the ratio of $(L_1)^2$ to $A_1$ and $(L_2)^2$ to $A_2$ is at least about 12:1, facilitates uniform heating of the nicotine source in the first compartment and the acid source in the second compartment throughout use of the cartridge.

Advantageously, providing an elongate first compartment having a length $L_1$ and a maximum transverse cross-sectional area $A_1$ and an elongate second compartment having a length $L_2$ and a maximum transverse cross-sectional area $A_2$, wherein the ratio of $(L_1)^2$ to $A_1$ and $(L_2)^2$ to $A_2$ is at least about 12:1, also facilitates vaporisation of nicotine from the nicotine source in the first compartment and the vaporisation of acid from the acid source in the second compartment.

Preferably, the ratio of $(L_1)^2$ to $A_1$ is between about 12:1 and about 400:1.

Preferably, the ratio of $(L_1)^2$ to $A_1$ is at least about 15:1.

Preferably, the ratio of $(L_1)^2$ to $A_1$ is between about 15:1 and about 200:1.

Preferably, the ratio of $(L_1)^2$ to $A_1$ is at least about 20:1.

Preferably, the ratio of $(L_1)^2$ to $A_1$ is between about 20:1 and about 100:1.

For example, the ratio of $(L_1)^2$ to $A_1$ may be between about 25:1 and about 70:1 or between about 30:1 and about 70:1.

Preferably, the ratio of $(L_2)^2$ to $A_2$ is between about 12:1 and about 400:1.

Preferably, the ratio of $(L_2)^2$ to $A_2$ is at least about 15:1.

Preferably, the ratio of $(L_2)^2$ to $A_2$ is between about 15:1 and about 200:1.

Preferably, the ratio of $(L_2)^2$ to $A_2$ is at least about 20:1.

Preferably, the ratio of $(L_2)^2$ to $A_2$ is between about 20:1 and about 100:1.

For example, the ratio of $(L_2)^2$ to $A_2$ may be between about 25:1 and about 70:1 or between about 30:1 and about 70:1.

As used herein with reference to the invention, the term "air inlet" is used to describe one or more apertures through which air may be drawn into a component or portion of a component of the cartridge.

As used herein with reference to the invention, the term "air outlet" is used to describe one or more apertures through which air may be drawn out of a component or portion of a component of the cartridge.

As used herein with reference to the invention, by "parallel" it is meant that the first compartment and the second compartment are arranged within the cartridge so that in use a first air stream drawn through the cartridge passes into the first compartment through the first air inlet, downstream through the first compartment and out of the first compartment through the first air outlet and a second air stream drawn through the cartridge passes into the second compartment through the second air inlet, downstream through the second compartment and out of the second compartment through the second air outlet. Nicotine vapour is released from the nicotine source in the first compartment into the first air stream drawn through the cartridge and acid vapour is released from the acid source in the second compartment into the second air stream drawn through the cartridge. The nicotine vapour in the first air stream reacts with the acid vapour in the second air stream in the gas phase to form an aerosol of nicotine salt particles.

As used herein with reference to the invention, the terms "proximal", "distal", "upstream" and "downstream" are used to describe the relative positions of components, or portions of components, of the cartridge and aerosol-generating system.

The aerosol-generating system according to the invention comprises a proximal end through which, in use, an aerosol of nicotine salt particles exits the aerosol-generating system for delivery to a user. The proximal end may also be referred to as the mouth end. In use, a user draws on the proximal end of the aerosol-generating system in order to inhale an aerosol generated by the aerosol-generating system. The aerosol-generating system comprises a distal end opposed to the proximal end.

When a user draws on the proximal end of the aerosol-generating system, air is drawn into the aerosol-generating system, passes through the cartridge and exits the aerosol-generating system at the proximal end thereof. Components, or portions of components, of the aerosol-generating system may be described as being upstream or downstream of one another based on their relative positions between the proximal end and the distal end of the aerosol-generating system.

The first air outlet of the first compartment of the cartridge is located at the proximal end of the first compartment of the cartridge. The first air inlet of the first compartment of the cartridge is located upstream of the first air outlet of the first compartment of the cartridge. The second air outlet of the second compartment of the cartridge is located at the proximal end of the second compartment of the cartridge. The second air inlet of the second compartment of the cartridge is located upstream of the second air outlet of the second compartment of the cartridge.

As used herein with reference to the invention, the term "longitudinal" is used to describe the direction between the proximal end and the opposed distal end of the cartridge or aerosol-generating system and the term "transverse" is used to describe the direction perpendicular to the longitudinal direction.

As used herein with reference to the invention, the term "length" is used to describe the maximum longitudinal dimension of components, or portions of components, of the cartridge or aerosol-generating system parallel to the longitudinal axis between the proximal end and the opposed distal end of the cartridge or aerosol-generating system.

As used herein with reference to the invention, the terms "height" and "width" are used to describe the maximum transverse dimensions of components, or portions of components, of the cartridge or aerosol-generating system perpendicular to the longitudinal axis of the cartridge or aerosol-generating system. Where the height and width of components, or portions of components, of the cartridge or aerosol-generating system are not the same, the term "width" is used to refer to the larger of the two transverse dimensions perpendicular to the longitudinal axis of the cartridge or aerosol-generating system.

As used herein with reference to the invention, the term "elongate" is used to describe a component or portion of a component of the cartridge having a length greater than the width and height thereof.

As described further below, by providing the nicotine source and the acid source in separate compartments with separate air inlets and separate air outlets, cartridges and aerosol-generating systems according to the present invention advantageously facilitate control of the reaction stoichiometry between the nicotine and the acid.

The ratio of nicotine and acid required to achieve an appropriate reaction stoichiometry may be controlled and balanced through variation of the volume of the first compartment relative to the volume of the second compartment.

The shape and dimensions of the first compartment of the cartridge may be chosen to allow a desired amount of nicotine to be housed in the cartridge.

The shape and dimensions of the second compartment of the cartridge may be chosen to allow a desired amount of acid to be housed in the cartridge.

The first compartment has a length $L_1$, a width $W_1$ and a height $H_1$ and the second compartment has a length $L_2$, a width $W_2$ and a height $H_2$. Advantageously, the ratio of $L_1$ to $W_1$ and $L_2$ to $W_2$ may be between about 2:1 and about 4:1, for example between about 5:2 and about 3:1. Advantageously, the ratio of $L_1$ to $H_1$ and $L_2$ to $H_2$ may be at least about 6:1.

Advantageously, the ratio of $L_1$ to $H_1$ and $L_2$ to $H_2$ may be between about 6:1 and about 30:1. Advantageously, the ratio of $L_1$ to $H_2$ and $L_2$ to $H_2$ may be between about 8:1 and about 16:1.

Advantageously, the first compartment of the cartridge has a length $L_1$ of between about 8 millimeters and about 40 millimeters, for example of between about 10 millimeters and about 20 millimeters. Advantageously, the first compartment of the cartridge has a width $W_1$ of between about 4 millimeters and about 6 millimeters. Advantageously, the first compartment of the cartridge has a height $H_1$ of between about 0.5 millimeters and about 2.5 millimeters.

The first compartment of the cartridge may have any suitable transverse cross-sectional shape. For example, the transverse cross-sectional shape of the first compartment may be circular, semi-circular, elliptical, triangular, square, rectangular or trapezoidal.

Advantageously, the second compartment of the cartridge has a length $L_2$ of between about 8 millimeters and about 40 millimeters, for example of between about 10 millimeters and about 20 millimeters. Advantageously, the second compartment of the cartridge has a width $W_2$ of between about 4 millimeters and about 6 millimeters. Advantageously, the second compartment of the cartridge has a height $H_2$ of between about 0.5 millimeters and about 2.5 millimeters.

The second compartment of the cartridge may have any suitable transverse cross-sectional shape. For example, the transverse cross-sectional shape of the second compartment may be circular, semi-circular, elliptical, triangular, square, rectangular or trapezoidal.

The shape and dimensions of the first compartment and the second compartment of the cartridge may be the same or different.

Advantageously, the ratio of the length of the first compartment $L_1$ to the length of the second compartment $L_2$ is between about 2:1 and about 1:2, more advantageously between about 1.2:1 and about 1:1.2.

Advantageously, the ratio of the maximum transverse cross-sectional area of the first compartment $A_1$ to the maximum transverse cross-sectional area of the first compartment $A_2$ is between about 2:1 and about 1:2, more advantageously between about 1.2:1 and about 1:1.2.

Advantageously, the shape and dimensions of the first compartment and the second compartment are substantially the same. Providing a first compartment and a second compartment having of substantially the same shape and dimensions may advantageously simplify manufacturing of the cartridge.

Advantageously, the first compartment of the cartridge contains a nicotine source comprising a first carrier material impregnated with between about 1 milligram and about 50 milligrams of nicotine.

As used herein with reference to the invention, the term "nicotine", is used to describe nicotine, nicotine base or a nicotine salt. In embodiments in which the first carrier material is impregnated with nicotine base or a nicotine salt, the amounts of nicotine recited herein are the amount of nicotine base or amount of ionised nicotine, respectively.

Advantageously, the first compartment of the cartridge contains a nicotine source comprising a first carrier material impregnated with between about 1 milligram and about 40 milligrams of nicotine.

Preferably, the first compartment of the cartridge contains a nicotine source comprising a first carrier material impregnated with between about 3 milligrams and about 30 milligrams of nicotine. More preferably, the first compartment of the cartridge contains a nicotine source comprising a first carrier material impregnated with between about 6 milligrams and about 20 milligrams of nicotine. Most preferably, the first compartment of the cartridge contains a nicotine source comprising a first carrier material impregnated with between about 8 milligrams and about 18 milligrams of nicotine.

The first carrier material may be impregnated with liquid nicotine or a solution of nicotine in an aqueous or non-aqueous solvent.

The first carrier material may be impregnated with natural nicotine or synthetic nicotine.

The acid source may comprise an organic acid or an inorganic acid.

Preferably, the acid source comprises an organic acid, more preferably a carboxylic acid, most preferably an alpha-keto or 2-oxo acid or lactic acid.

Advantageously, the acid source comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid, lactic acid and combinations thereof. Advantageously, the acid source comprises pyruvic acid or lactic acid. More advantageously, the acid source comprises lactic acid.

Advantageously, the second compartment of the cartridge contains an acid source comprising a second carrier material impregnated with acid.

The first carrier material and the second carrier material may be the same or different.

Advantageously, the first carrier material and the second carrier material have a density of between about 0.1 grams/cubic centimeter and about 0.3 grams/cubic centimeter.

Advantageously, the first carrier material and the second carrier material have a porosity of between about 15 percent and about 55 percent.

The first carrier material and the second carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The first carrier material acts as a reservoir for the nicotine.

Advantageously, the first carrier material is chemically inert with respect to nicotine.

The first carrier material may have any suitable shape and size. For example, the first carrier material may be in the form of a sheet or plug.

Advantageously, the shape and of the first carrier material is similar to the shape and size of the first compartment of the cartridge.

The shape, size, density and porosity of the first carrier material may be chosen to allow the first carrier material to be impregnated with a desired amount of nicotine.

Advantageously, the first compartment of the cartridge may further comprise a flavourant. Suitable flavourants include, but are not limited to, menthol.

Advantageously, the first carrier material may be impregnated with between about 3 milligrams and about 12 milligrams of flavourant.

The second carrier material acts as a reservoir for the acid.

Advantageously, the second carrier material is chemically inert with respect to the acid.

The second carrier material may have any suitable shape and size. For example, the second carrier material may be in the form of a sheet or plug.

Advantageously, the shape and size of the second carrier material is similar to the shape and size of the second compartment of the cartridge.

The shape, size, density and porosity of the second carrier material may be chosen to allow the second carrier material to be impregnated with a desired amount of acid.

Advantageously, the second compartment of the cartridge contains a lactic acid source comprising a second carrier material impregnated with between about 2 milligrams and about 60 milligrams of lactic acid.

Preferably, the second compartment of the cartridge contains a lactic acid source comprising a second carrier material impregnated with between about 5 milligrams and about 50 milligrams of lactic acid. More preferably, the second compartment of the cartridge contains a lactic acid source comprising a second carrier material impregnated with between about 8 milligrams and about 40 milligrams of lactic acid. Most preferably, the second compartment of the cartridge contains a lactic acid source comprising a second carrier material impregnated with between about 10 milligrams and about 30 milligrams of lactic acid.

The shape and dimensions of the first compartment of the cartridge may be chosen to allow a desired amount of nicotine to be housed in the cartridge.

The shape and dimensions of the second compartment of the cartridge may be chosen to allow a desired amount of acid to be housed in the cartridge.

The ratio of nicotine and acid required to achieve an appropriate reaction stoichiometry may be controlled and balanced through variation of the volume of the first compartment relative to the volume of the second compartment.

The first air inlet of the first compartment of the cartridge and the second air inlet of the second compartment of the cartridge may each comprise one or more apertures. For example, the first air inlet of the first compartment of the cartridge and the second air inlet of the second compartment of the cartridge may each comprise one, two, three, four, five, six or seven apertures.

The first air inlet of the first compartment of the cartridge and the second air inlet of the second compartment of the cartridge may comprise the same or different numbers of apertures.

Advantageously, the first air inlet of the first compartment of the cartridge and the second air inlet of the second compartment of the cartridge each comprise a plurality of apertures. For example, the first air inlet of the first compartment of the cartridge and the second air inlet of the second compartment of the cartridge may each comprise two, three, four, five, six or seven apertures.

Providing a first compartment having a first air inlet comprising a plurality of apertures and a second compartment having a second air inlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

The ratio of nicotine and acid required to achieve an appropriate reaction stoichiometry may be controlled and balanced through variation of the volumetric airflow through the first compartment of the cartridge relative to the volumetric airflow through the second compartment of the cartridge. The ratio of the volumetric airflow through the first compartment relative to the volumetric airflow through the second compartment may be controlled through variation of one or more of the number, dimensions and location of the apertures forming the first air inlet of the first compartment of the cartridge relative to the number, dimensions and location of the apertures forming the second air inlet of the second compartment of the cartridge.

In embodiments in which the acid source comprises lactic acid, advantageously the flow area of the second air inlet of the second compartment of the cartridge is greater than the flow area of the first air inlet of the first compartment of the cartridge.

As used herein with reference to the invention, the term "flow area" is used to describe the cross-sectional area of an air inlet or air outlet through which air flows during use. In embodiments in which an air inlet or air outlet comprises a plurality of apertures, the flow area of the air inlet or air outlet is the total flow area of the air inlet or air outlet and is equal to the sum of the flow areas of each of the plurality of apertures forming the air inlet or air outlet. In embodiments in which the cross-sectional area of an air inlet or air outlet varies in the direction of airflow, the flow area of the air inlet or air outlet is the minimum cross-sectional area in the direction of airflow.

Increasing the flow area of the second air inlet of the second compartment of the cartridge relative to the flow area of the first air inlet of the first compartment of the cartridge advantageously increases the volumetric airflow through the second air inlet compared to the volumetric airflow through the first air inlet.

In embodiments in which the acid source comprises lactic acid, preferably the ratio of the flow area of the first air inlet of the first compartment of the cartridge to the flow area of the second air inlet of the second compartment of the cartridge is between about 3:4 and about 1:2. More preferably, the ratio of the flow area of the first air inlet of the first compartment of the cartridge to the flow area of the second air inlet of the second compartment of the cartridge is between about 2:3 and about 1:2.

The flow area of the second air inlet of the second compartment of the cartridge may be increased relative to the flow area of the first air inlet of the first compartment of the cartridge by one or both of increasing the size of the one or more apertures forming the second air inlet relative to the size of the one or more apertures forming the first air inlet and increasing the number of apertures forming the second air inlet relative to the number of apertures forming the first air inlet.

Advantageously, the flow area of the second air inlet of the second compartment of the cartridge is increased relative to the flow area of the first air inlet of the first compartment of the cartridge by increasing the number of apertures forming the second air inlet relative to the number of apertures forming the first air inlet.

Advantageously, the first air inlet of the first compartment of the cartridge comprises between 2 and 5 apertures.

Advantageously, the second air inlet of the second compartment of the cartridge comprises between 3 and 7 apertures.

Advantageously, the flow area of the first air inlet of the first compartment of the cartridge is between about 0.1 square millimeters and about 1.6 square millimeters, more advantageously between about 0.2 square millimeters and about 0.8 square millimeters.

In embodiments in which the first air inlet of the first compartment of the cartridge comprises a plurality of apertures, the apertures may have different flow areas so that the flow area of the first air inlet of the first compartment of the cartridge is divided unequally between the apertures forming the first air inlet.

In embodiments in which the first air inlet of the first compartment of the cartridge comprises a plurality of apertures, each of the apertures may have the same flow area so that the flow area of the first air inlet of the first compartment of the cartridge is divided equally between the apertures forming the first air inlet. Providing a first compartment having a first air inlet comprising a plurality of apertures having substantially the same flow area may advantageously simplify manufacturing of the cartridge.

The first air inlet of the first compartment of the cartridge may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimeters and about 0.6 millimeters.

In embodiments in which the acid source comprises lactic acid, advantageously the flow area of the second air inlet of the second compartment of the cartridge is between about 0.2 square millimeters and about 2.4 square millimeters, more advantageously between about 0.4 square millimeters and about 1.2 square millimeters.

In embodiments in which the second air inlet of the second compartment of the cartridge comprises a plurality of apertures, the apertures may have different flow areas so that the total flow area of the second air inlet of the second compartment of the cartridge is divided unequally between the apertures forming the second air inlet.

In embodiments in which the second air inlet of the second compartment of the cartridge comprises a plurality of apertures, each of the apertures may have the same flow area so that the total flow area of the second air inlet of the second compartment of the cartridge is divided equally between the apertures forming the second air inlet. Providing a second compartment having a second air inlet comprising a plurality of apertures having substantially the same flow area may advantageously simplify manufacturing of the cartridge.

The second air inlet of the second compartment of the cartridge may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimeters and about 0.6 millimeters.

Advantageously, the first compartment has a longitudinal first air inlet and the second compartment has a longitudinal second air inlet.

As used herein with reference to the invention, the term "longitudinal air inlet" is used to describe one or more apertures through which air may be drawn in a longitudinal direction into a component or portion of a component of the cartridge.

Advantageously, prior to first use of the cartridge, one or both of the first air inlet of the first compartment and the second air inlet of the second compartment may be sealed by one or more removable or frangible barriers. For example, one or both of the first air inlet of the first compartment and the second air inlet of the second compartment may be sealed by one or more peel-off or pierceable seals.

The one or more removable or frangible barriers may be formed from any suitable material. For example, the one or more removable or frangible barriers may be formed from a metal foil or film.

The first air outlet of the first compartment of the cartridge and the second air outlet of the second compartment of the cartridge may each comprise one or more apertures. For example, the first air outlet of the first compartment of the cartridge and the second air outlet of the second compartment of the cartridge may each comprise one, two, three, four, five, six or seven apertures.

The first air outlet of the first compartment of the cartridge and the second air outlet of the second compartment of the cartridge may comprise the same or different numbers of apertures.

Advantageously, the first air outlet of the first compartment of the cartridge and the second air outlet of the second compartment of the cartridge may each comprise a plurality of apertures. For example, the first air outlet of the first compartment of the cartridge and the second air outlet of the second compartment of the cartridge may each comprise two, three, four, five, six or seven apertures. Providing a first compartment having a first air outlet comprising a plurality of apertures and a second compartment having a second air outlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

In embodiments in which the first air outlet of the first compartment of the cartridge comprises a plurality of apertures, advantageously the first air outlet comprises between 2 and 5 apertures.

In embodiments in which the second air outlet of the second compartment of the cartridge comprises a plurality of apertures, advantageously, the second air outlet comprises between 3 and 7 apertures.

Advantageously, the first air outlet of the first compartment of the cartridge of the cartridge assembly and the second air outlet of the second compartment of the cartridge of the cartridge assembly may each comprise a single aperture. Providing a first compartment having a first air outlet comprising a single aperture and a second compartment having a second air outlet comprising a single aperture may advantageously simplify manufacturing of the cartridge.

The ratio of nicotine and acid required to achieve an appropriate reaction stoichiometry may be controlled and balanced through variation of the volumetric airflow through the first compartment of the cartridge relative to the volumetric airflow through the second compartment of the cartridge. The ratio of the volumetric airflow through the first compartment relative to the volumetric airflow through the second compartment may be controlled through variation of one or more of the number, dimensions and location of the apertures forming the first air outlet of the first compartment of the cartridge relative to the number, dimensions and location of the apertures forming the second air outlet of the second compartment of the cartridge.

The flow area of the first air outlet of the first compartment may be the same as or different to the flow area of the second air outlet of the second compartment of the cartridge.

The flow area of the second air outlet of the second compartment of the cartridge may be greater than flow area of the first air outlet of the first compartment of the cartridge.

Increasing the flow area of the second air outlet of the second compartment of the cartridge relative to the flow area of the first air outlet of the first compartment of the cartridge may advantageously increase the volumetric airflow through the second air outlet compared to the volumetric airflow through the first air outlet.

In embodiments in which the acid source comprises lactic acid, the ratio of the flow area of the first air outlet of the first compartment of the cartridge to the flow area of the second air outlet of the second compartment of the cartridge is preferably between about 3:4 and about 1:2. More preferably, the ratio of the flow area of the first air outlet of the first compartment of the cartridge to the flow area of the second air outlet of the second compartment of the cartridge is between about 2:3 and about 1:2.

In embodiments in which the flow area of the second air outlet of the second compartment of the cartridge is greater than flow area of the first air outlet of the first compartment of the cartridge, the flow area of the second air outlet of the second compartment of the cartridge may be increased relative to the flow area of the first air outlet of the first compartment of the cartridge by one or both of increasing the size of the one or more apertures forming the second air outlet relative to the size of the one or more apertures forming the first air outlet and increasing the number of apertures forming the second air outlet relative to the number of apertures forming the first air outlet.

Advantageously, the flow area of the second air outlet of the second compartment of the cartridge is increased relative to the flow area of the first air outlet of the first compartment of the cartridge by increasing the number of apertures forming the second air outlet relative to the number of apertures forming the first air outlet.

The first air inlet and the first air outlet of the first compartment of the cartridge may comprise the same or different numbers of apertures.

Advantageously, the first air inlet and the first air outlet of the first compartment of the cartridge comprise the same numbers of apertures. Providing a first compartment having a first air inlet and a first air outlet comprising the same number of apertures may advantageously simplify manufacturing of the cartridge.

The second air inlet and the second air outlet of the second compartment of the cartridge may comprise the same or different numbers of apertures.

Advantageously, the second air inlet and the second air outlet of the second compartment of the cartridge comprise the same numbers of apertures. Providing a second compartment having a second air inlet and a second air outlet comprising the same number of apertures may advantageously simplify manufacturing of the cartridge.

Advantageously, the flow area of the first air outlet of the first compartment of the cartridge is between about 0.1 square millimeters and about 5 square millimeters.

In embodiments in which the first air outlet of the first compartment of the cartridge comprises a plurality of apertures, the apertures may have different flow areas so that the flow area of the first air outlet of the first compartment of the cartridge is divided unequally between the apertures forming the first air outlet.

In embodiments in which the first air outlet of the first compartment of the cartridge comprises a plurality of apertures, each of the apertures may have the same flow area so that the flow area of the first air outlet of the first compartment of the cartridge is divided equally between the apertures forming the first air outlet. Providing a first compartment having a first air outlet comprising a plurality of apertures having substantially the same flow area may advantageously simplify manufacturing of the cartridge.

The first air outlet of the first compartment of the cartridge may comprise one or more apertures having any suitable cross-sectional shape. For example, the cross-sectional shape of each aperture may be circular, elliptical, square or rectangular. In embodiments in which the first air outlet of the first compartment of the cartridge comprises a plurality of apertures, advantageously each aperture has a substantially circular cross-sectional shape. In such embodiments, advantageously the diameter of each aperture is between about 0.2 millimeters and about 0.6 millimeters.

The dimensions of the one or more apertures forming the first air inlet of the first compartment of the cartridge may be the same as or different to the dimensions of the one or more apertures forming the first air outlet of the first compartment of the cartridge.

Advantageously, the dimensions of the one or more apertures forming the first air inlet of the first compartment of the cartridge may be substantially the same as the dimensions of the one or more apertures forming the first air outlet of the first compartment of the cartridge. Providing a first compartment having a first air inlet and a first air outlet comprising one or more apertures of substantially the same dimensions may advantageously simplify manufacturing of the cartridge.

Advantageously, the dimensions of the one or more apertures forming the first air outlet of the first compartment of the cartridge may be greater than the dimensions of the one or more apertures forming the first air inlet of the first compartment of the cartridge. Increasing the dimensions of the apertures forming the first air outlet of the first compartment of the cartridge relative to the dimensions of the apertures forming the first air inlet of the first compartment of the cartridge may advantageously reduce the risk of the first air outlet of the first compartment of the cartridge becoming obstructed by, for example, dust.

Advantageously, the flow area of the second air outlet of the second compartment of the cartridge is between about 0.1 square millimeters and about 5 square millimeters.

In embodiments in which the second air outlet of the second compartment of the cartridge comprises a plurality of apertures, the apertures may have different flow areas so that the total flow area of the second air outlet of the second compartment of the cartridge is divided unequally between the apertures forming the second air outlet.

In embodiments in which the second air outlet of the second compartment of the cartridge comprises a plurality of apertures, each of the apertures may have the same flow area so that the total flow area of the second air outlet of the second compartment of the cartridge is divided equally between the apertures forming the second air outlet. Providing a second compartment having a second air outlet comprising a plurality of apertures having substantially the same flow area may advantageously simplify manufacturing of the cartridge.

The second air outlet of the second compartment of the cartridge may comprise one or more apertures having any suitable cross-sectional shape. For example, the cross-sectional shape of each aperture may be circular, elliptical, square or rectangular. In embodiments in which the second air outlet of the second compartment of the cartridge comprises a plurality of apertures, advantageously each aperture has a substantially circular cross-sectional shape. In such embodiments, advantageously the diameter of each aperture is between about 0.2 millimeters and about 0.6 millimeters.

The dimensions of the one or more apertures forming the second air inlet of the second compartment of the cartridge may be the same as or different to the dimensions of the one or more apertures forming the second air outlet of the second compartment of the cartridge.

Advantageously, the dimensions of the one or more apertures forming the second air inlet of the second compartment of the cartridge may be substantially the same as the dimensions of the one or more apertures forming the second air outlet of the second compartment of the cartridge. Providing a second compartment having a second air inlet and a second air outlet comprising one or more apertures of substantially the same dimensions may advantageously simplify manufacturing of the cartridge.

Advantageously, the dimensions of the one or more apertures forming the second air outlet of the second compartment of the cartridge may be greater than the dimensions of the one or more apertures forming the second air inlet of the second compartment of the cartridge. Increasing the dimensions of the apertures forming the second air outlet of the second compartment of the cartridge relative to the dimensions of the apertures forming the second air inlet of the second compartment of the cartridge may advantageously reduce the risk of the second air outlet of the second compartment of the cartridge becoming obstructed by, for example, dust.

Advantageously, the first compartment has a longitudinal first air outlet and the second compartment has a longitudinal second air outlet.

As used herein with reference to the invention, the term "longitudinal air outlet" is used to describe one or more apertures through which air may be drawn in a longitudinal direction out of a component or portion of a component of the cartridge.

Advantageously, prior to first use of the cartridge, one or both of the first air outlet of the first compartment and the second air outlet of the second compartment may be sealed by one or more removable or frangible barriers. For example, one or both of the first air outlet of the first compartment and the second air outlet of the second compartment may be sealed by one or more peel-off or pierceable seals.

The one or more removable or frangible barriers may be formed from any suitable material. For example, the one or more removable or frangible barriers may be formed from a metal foil or film.

Advantageously, prior to first use of the cartridge, the first air inlet and the first air outlet of the first compartment of the cartridge and the second air inlet and the second air outlet of the second compartment of the cartridge are sealed by one or more removable or frangible barriers.

The cartridge may further comprise a third compartment downstream of the first compartment and the second compartment and in fluid communication with the first air outlet of the first compartment and the second air outlet of the second compartment. The nicotine vapour in the first air stream may react with the acid vapour in the second air stream in the third compartment to form an aerosol of nicotine salt particles.

In embodiments in which the cartridge further comprises a third compartment, the third compartment may comprise one or more aerosol-modifying agents. For example, the third compartment may comprise one or more sorbents, one or more flavourants, one or more chemesthetic agents or a combination thereof.

The first compartment and the second compartment may be arranged symmetrically with respect to each other within the cartridge.

Advantageously, the cartridge is an elongate cartridge. In embodiments in which the cartridge is an elongate cartridge, the first compartment and the second compartment of the cartridge may be arranged symmetrically about the longitudinal axis of the cartridge.

The cartridge may have any suitable shape. For example, the cartridge may be substantially cylindrical.

The cartridge may have any suitable transverse cross-sectional shape. For example, the transverse cross-sectional shape of the cartridge may be circular, semi-circular, elliptical, triangular, square, rectangular or trapezoidal.

The cartridge may have any suitable size.

For example, the cartridge may have a length of between about 5 millimeters and about 50 millimeters. Advantageously, the cartridge may have a length between about 10 millimeters and about 20 millimeters.

For example, the cartridge may have a width of between about 4 millimeters and about 10 millimeters and a height of between about 4 millimeters and about 10 millimeters. Advantageously, the cartridge may have a width of between about 6 millimeters and about 8 millimeters and a height of between about 6 millimeters and about 8 millimeters.

Advantageously, the cartridge comprises a body portion and one or more end caps.

The cartridge may comprise a body portion and a distal end cap.

The cartridge may comprise a body portion and a proximal end cap.

The cartridge may comprise a body portion, a distal end cap and a proximal end cap.

In embodiments in which the cartridge comprises a distal end cap, one or more apertures forming the first air inlet of the first compartment of the cartridge and one or more apertures forming the second air inlet of the second compartment of the cartridge may be provided in the distal end cap.

In embodiments in which the cartridge comprises a proximal end cap, one or more apertures forming the first air outlet of the first compartment of the cartridge and one or more apertures forming the second air outlet of the second compartment of the cartridge may be provided in the proximal end cap.

The cartridge may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

In embodiments in which the cartridge comprises a body portion and one or more end caps, the body portion and the one or more end caps may be formed from the same or different materials.

The cartridge may be formed from one or more materials that are nicotine-resistant and acid-resistant.

The first compartment of the cartridge may be coated with one or more nicotine-resistant materials and the second compartment of the cartridge may be coated with one or more acid-resistant materials.

Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins and combinations thereof.

Use of one or more nicotine-resistant materials to one or both of form the cartridge and coat the interior of the first compartment of the cartridge may advantageously enhance the shelf life of the cartridge.

Use of one or more acid-resistant materials to one or both of form the cartridge and coat the interior of the second compartment of the cartridge may advantageously enhance the shelf life of the cartridge.

The cartridge may be formed from one or more thermally conductive materials.

The first compartment of the cartridge and the second compartment of the cartridge may be coated with one or more thermally conductive materials.

Use of one or more thermally conductive materials to one or both of form the cartridge and coat the interior of the first compartment and the second compartment of the cartridge may advantageously increase heat transfer from a heater to the nicotine source and the acid source.

Suitable thermally conductive materials include, but are not limited to, metals such as, for example, aluminium chromium, copper, gold, iron, nickel and silver, alloys, such as brass and steel and combinations thereof.

The cartridge may be formed of one or more materials having a low resistivity or a high resistivity depending on whether the first compartment and the second compartment are heated by conduction or induction.

The first compartment of the cartridge and the second compartment of the cartridge may be coated with one or more materials having a low resistivity or a high resistivity depending on whether the first compartment and the second compartment are heated by conduction or induction.

The cartridge may be formed by any suitable method. Suitable methods include, but are not limited to, deep drawing, injection moulding, blistering, blow forming and extrusion.

The cartridge may be designed to be disposed of once the nicotine in the first compartment and the acid in the second compartment are depleted.

The cartridge may be designed to be refillable.

Advantageously, the cartridge may comprise a heater configured to heat the first compartment and the second compartment. In such embodiments, the heater is advantageously located between the first compartment and the second compartment. That is the first compartment and the second compartment are disposed on either side of the heater.

The heater may be an electrical heater. The heater may be a resistive heater.

Advantageously, the heater is configured to heat the first compartment and the second compartment of the cartridge to a temperature of below about 250 degrees Celsius. Preferably, the heater is configured to heat the first compartment and the second compartment of the cartridge to a temperature of between about 80 degrees Celsius and about 150 degrees Celsius.

Advantageously, the heater is configured to heat the first compartment and the second compartment of the cartridge to substantially the same temperature.

As used herein with reference to the invention, by "substantially the same temperature" it is meant that the difference in temperature between the first compartment and the second compartment of the cartridge measured at corresponding locations relative to the heater is less than about 3° C.

In use, heating the first compartment and the second compartment of the cartridge to a temperature above ambient temperature advantageously enables the vapour concentrations of the nicotine in the first compartment of the cartridge and the vapour pressure of acid in the second compartment of the cartridge to be controlled and balanced proportionally to yield an efficient reaction stoichiometry between the nicotine and the acid. Advantageously, this may improve the efficiency of the formation of nicotine salt particles and the consistency of delivery to a user. Advantageously, it may also reduce the delivery of unreacted nicotine and unreacted acid to a user.

According to the invention there is further provided an aerosol-generating system comprising: a cartridge according to the invention comprising a heater configured to heat the first compartment and the second compartment; and an aerosol-generating device comprising: a housing defining a cavity for receiving at least a portion of the cartridge; and a power supply configured to supply power to the heater of the cartridge.

The aerosol-generating system may further comprise a mouthpiece. In such embodiments, nicotine vapour released from the nicotine source in the first compartment of the cartridge and acid vapour released from the acid source in the second compartment of the cartridge may react with one another in the gas phase in the mouthpiece to form an aerosol of nicotine salt particles.

The mouthpiece may be configured for engagement with the cartridge.

In embodiments in which the mouthpiece is configured for engagement with the cartridge, the combination of the cartridge and the mouthpiece may simulate the shape and dimensions of a combustible smoking article, such as a cigarette, a cigar, or a cigarillo. Advantageously, in such embodiments the combination of the cartridge and the mouthpiece may simulate the shape and dimensions of a cigarette.

The mouthpiece may be configured for engagement with the housing of the aerosol-generating device.

The mouthpiece may be designed to be disposed of once the nicotine in the first compartment and the acid in the second compartment are depleted.

The mouthpiece may be designed to be reusable. In embodiments in which the mouthpiece is designed to be reusable, the mouthpiece may advantageously be configured to be removably attached to the cartridge or the housing of the aerosol-generating device.

Advantageously the cartridge may comprise a cavity for receiving a heater configured to heat the first compartment and the second compartment. In such embodiments, the cavity is advantageously located between the first compartment and the second compartment. That is the first compartment and the second compartment are disposed on either side of the cavity.

Advantageously, the cavity extends from the distal end of the cartridge at least part way along the length of the cartridge.

Advantageously, the cavity extends along the longitudinal axis of the cartridge.

The cavity may extend from the distal end of the cartridge to the proximal end of the cartridge. In such embodiments, the cavity has an open distal end and an open proximal end.

The cavity may extend from the distal end of the cartridge part way along the length of the cartridge. In such embodiments, the cavity has an open distal end and a closed proximal end.

The cavity may be enclosed along its length.

The cavity may be at least partially open along its length. This may advantageously facilitate insertion of a heater into the cavity.

Advantageously, the cartridge may comprise a susceptor for inductively heating the first compartment and the second compartment. In such embodiments, the susceptor is advantageously located between the first compartment and the second compartment. That is the first compartment and the second compartment are disposed on either side of the susceptor.

According to the invention there is provided an aerosol-generating system comprising: a cartridge according to the invention; and an aerosol-generating device comprising: a housing defining a cavity for receiving at least a portion of the cartridge; and a heater for heating the first compartment and the second compartment of the cartridge.

Advantageously, the aerosol-generating system comprises a consumable cartridge assembly according to the invention and a reusable aerosol-generating device comprising a heater for heating the first compartment and the second compartment of the cartridge.

The heater may be an electrical heater. The heater may be a resistive heater.

Advantageously, the heater is configured to heat the first compartment and the second compartment of the cartridge to a temperature of below about 250 degrees Celsius. Preferably, the heater is configured to heat the first compartment and the second compartment of the cartridge to a temperature of between about 80 degrees Celsius and about 150 degrees Celsius.

Advantageously, the heater is configured to heat the first compartment and the second compartment of the cartridge to substantially the same temperature.

As used herein with reference to the invention, by "substantially the same temperature" it is meant that the difference in temperature between the first compartment and the second compartment of the cartridge measured at corresponding locations relative to the heater is less than about 3° C.

The heater may be arranged to circumscribe at least a portion of the cartridge when the cartridge is received within the cavity.

Advantageously, the heater may be located within the cavity of the aerosol-generating device and the cartridge may comprise a cavity for receiving the heater as described above. In such embodiments, the heater of the aerosol-generating device may advantageously be an elongate heater in the form of a heater blade having a width that is greater than the thickness thereof and the cavity in the cartridge may be configured as an elongate slot.

Advantageously, the heater may be an inductive heater and the cartridge may comprise a susceptor for inductively heating the first compartment and the second compartment of the cartridge as described above.

The aerosol-generating system may further comprise a power supply for supplying power to the heater and a controller configured to control a supply of power from the power supply to the heater.

The aerosol-generating device may comprise one or more temperature sensors configured to sense the temperature of the heater and the temperature of the first compartment and the second compartment of the cartridge. In such embodiments, the controller may be configured to control a supply of power to the heater based on the sensed temperature.

The aerosol-generating system may further comprise a mouthpiece. In such embodiments, nicotine vapour released from the nicotine source in the first compartment of the cartridge and acid vapour released from the acid source in the second compartment of the cartridge may react with one another in the gas phase in the mouthpiece to form an aerosol of nicotine salt particles.

The mouthpiece may be configured for engagement with the cartridge.

In embodiments in which the mouthpiece is configured for engagement with the cartridge, the combination of the cartridge and the mouthpiece may simulate the shape and dimensions of a combustible smoking article, such as a cigarette, a cigar, or a cigarillo. Advantageously, in such embodiments the combination of the cartridge and the mouthpiece may simulate the shape and dimensions of a cigarette.

The mouthpiece may be configured for engagement with the housing of the aerosol-generating device.

The mouthpiece may be designed to be disposed of once the nicotine in the first compartment and the acid in the second compartment are depleted.

The mouthpiece may be designed to be reusable. In embodiments in which the mouthpiece is designed to be reusable, the mouthpiece may advantageously be configured to be removably attached to the cartridge or the housing of the aerosol-generating device.

For the avoidance of doubt, features described above in relation to one aspect of the invention may also be applicable to other aspects of the invention. In particular, features described above in relation to the cartridge of the invention may also relate, where appropriate, to the aerosol-generating systems of the invention, and vice versa.

Embodiments of the invention will now be described, by way of example only, with reference to the accompanying drawings, in which:

FIGS. 1A-1H show schematic illustrations of an elongate cartridge 2 according to a first embodiment of the invention for use in an aerosol-generating system for generating an aerosol comprising nicotine lactate salt particles.

The cartridge 2 has a length of about 15 millimeters, a width of about 7 millimeters and a height of about 5.2 millimeters. The cartridge 2 comprises an elongate body 4, a distal end cap 6 and a proximal end cap 8.

The body 4 has a length of about 13 millimeters, a width of about 7 millimeters and a height of about 5.2 millimeters. The distal end cap 6 and the proximal end cap 8 have a length of about 2 millimeters, a width of about 7 millimeters and a height of about 5.2 millimeters.

The cartridge 2 comprises an elongate first compartment 10 that extends from the proximal end of the body 4 to the distal end of the body 4. The first compartment 10 contains a nicotine source comprising a first carrier material 12 impregnated with about 10 milligrams of nicotine and about 4 milligrams of menthol.

The cartridge 2 comprises an elongate second compartment 14 that extends from the proximal end of the body 4 to the distal end of the body 4. The second compartment 14 contains a lactic acid source comprising a second carrier material 16 impregnated with about 20 milligrams of lactic acid.

The first compartment 10 and the second compartment 14 are arranged in parallel.

The cartridge 2 further comprises a cavity 18 for receiving a heater configured to heat the first compartment 10 and the second compartment 14. The cavity 18 is located between the first compartment 10 and the second compartment 14 and extends from the proximal end of the body 4 to the distal end of the body 4. The cavity 18 is of substantially stadium shaped transverse cross-section and has a width of about 6.3 millimeters and a height of about 1 millimeter.

The distal end cap 6 comprises a first air inlet 20 comprising a row of three spaced apart apertures and a second air inlet 22 comprising a row of five spaced apart apertures. Each of the apertures forming the first air inlet 20 and the second air inlet 22 is of substantially circular transverse cross-section and has a diameter of about 0.3 millimeters.

The flow area of the first air inlet 20 is about 0.21 square millimeters and the flow area of the second air inlet 22 is about 0.35 square millimeters. The ratio of the flow area of the first air inlet 20 to the flow area of the second air inlet 22 is about 3:5.

The distal end cap 6 further comprises a third inlet 24 located between the first air inlet 20 and the second air inlet 22. The third inlet 24 is of substantially stadium shaped transverse cross-section and has a width of about 6.3 millimeters and a height of about 1 millimeter.

The proximal end cap 8 comprises a first air outlet 26 comprising a row of three spaced apart apertures and a second air outlet 28 comprising a row of five spaced apart apertures. Each of the apertures forming the first air outlet 26 and the second air outlet 28 is of substantially circular transverse cross-section and has a diameter of about 0.3 millimeters.

The flow area of the first air outlet 26 is about 0.21 square millimeters and the flow area of the second air outlet 28 is about 0.35 square millimeters. The ratio of the flow area of the first air outlet 26 to the flow area of the second air outlet 28 is about 3:5.

As shown in FIGS. 1A-1H, to form the cartridge 2, the proximal end cap 8 is inserted into the proximal end of the body 4 such that the first air outlet 26 is aligned with the first compartment 10 and the second air outlet 28 is aligned with the second compartment 14.

The first carrier material 12 impregnated with nicotine and menthol is inserted into the first compartment 10 and the second carrier material 16 impregnated with lactic acid is inserted into the second compartment 14.

The distal end cap 6 is then inserted into the distal end of the body 4 such that the first air inlet 20 is aligned with the first compartment 10, the second air inlet 22 is aligned with the second compartment 14 and the third inlet 24 is aligned with the cavity 18.

The first compartment 10 and the second compartment 14 are substantially the same shape and size. The first compartment 10 and the second compartment 14 are of substantially rectangular transverse cross-section and have a length of about 11 millimeters, a width of about 4.3 millimeters and a height of about 1 millimeters.

The first carrier material 12 and the second carrier material 16 comprise a non-woven sheet of PET/PBT and are substantially the same shape and size. The shape and size of the first carrier material 12 and the second carrier material 16 is similar to the shape and size of the first compartment 10 and the second compartment 14 of the cartridge 2, respectively.

The first air inlet 20 is in fluid communication with the first air outlet 26 so that a first air stream may pass into the cartridge 2 through the first air inlet 20, through the first compartment 10 and out of the cartridge 2 though the first air outlet 26. The second air inlet 22 is in fluid communication with the second air outlet 28 so that a second air stream may pass into the cartridge 2 through the second air inlet 22, through the second compartment 14 and out of the cartridge 2 though the second air outlet 28.

Prior to first use of the cartridge 2, the first air inlet 20 and the second air inlet 22 may be sealed by a removable peel-off foil seal or a pierceable foil seal (not shown) applied to the external face of the distal end cap 6. Similarly, prior to first use of the cartridge 2, the first air outlet 26 and the second air outlet 28 may be sealed by a removable peel-off foil seal or a pierceable foil seal (not shown) applied to the external face of the proximal end cap 8.

FIGS. 2A-2E show schematic illustrations of an elongate cartridge 102 according to a second embodiment of the invention for use in an aerosol-generating system for generating an aerosol comprising nicotine lactate salt particles.

The cartridge 102 has a length of about 15 millimeters, a width of about 7.1 millimeters and a height of about 6.75 millimeters. The cartridge 102 comprises an elongate body 104 and a distal end cap 106.

The body 104 has a length of about 13 millimeters, a width of about 7.1 millimeters and a height of about 6.75 millimeters. The body 104 has a proximal end wall 108. The distal end cap 106 has a length of about 2 millimeters, a width of about 7.1 millimeters and a height of about 6.75 millimeters.

The cartridge 102 comprises an elongate first compartment 110 that extends from the distal end of the body 104 to the proximal end wall 108 of the body 104. The first compartment 110 contains a nicotine source comprising a first carrier material 112 impregnated with about 10 milligrams of nicotine and about 4 milligrams of menthol.

The cartridge 102 comprises an elongate second compartment 114 that extends from the distal end of the body 104 to the proximal end wall 108 of the body 104. The second compartment 114 contains a lactic acid source comprising a second carrier material 116 impregnated with about 20 milligrams of lactic acid.

The first compartment 110 and the second compartment 114 are arranged in parallel.

The cartridge 102 further comprises a cavity 118 for receiving a heater configured to heat the first compartment 110 and the second compartment 114. The cavity 118 is located between the first compartment 110 and the second compartment 114 and extends from the distal end of the body 1044 to the proximal end wall 108 of the body 104. The cavity 118 is of substantially rectangular transverse cross-section and has a width of about 6 millimeters and a height of about 1 millimeter.

The distal end cap 106 comprises a first air inlet 120 comprising a row of three spaced apart apertures and a second air inlet 122 comprising a row of five spaced apart apertures. Each of the apertures forming the first air inlet 120 and the second air inlet 122 is of substantially circular transverse cross-section and has a diameter of about 0.5 millimeters.

The flow area of the first air inlet 120 is about 0.59 square millimeters and the flow area of the second air inlet 122 is about 0.98 square millimeters. The ratio of the flow area of the first air inlet 120 to the flow area of the second air inlet 122 is about 3:5.

The distal end cap 106 further comprises a third inlet 124 located between the first air inlet 120 and the second air inlet 122. The third inlet 124 is of substantially rectangular transverse cross-section and has a width of about 6 millimeters and a height of about 1 millimeter.

The proximal end wall 108 of the body 104 comprises a first air outlet 126 comprising a row of three spaced apart apertures and a second air outlet 128 comprising a row of five spaced apart apertures. The first air outlet 126 is aligned with the first compartment 110 and the second air outlet 128 is aligned with the second compartment 114. Each of the apertures forming the first air outlet 126 and the second air outlet 128 is of substantially circular transverse cross-section and has a diameter of about 0.5 millimeters.

The flow area of the first air outlet 126 is about 0.59 square millimeters and the flow area of the second air outlet 128 is about 0.98 square millimeters. The ratio of the flow area of the first air outlet 126 to the flow area of the second air outlet 128 is about 3:5.

As shown in FIGS. 2A-2E, to form the cartridge 102, the first carrier material 112 impregnated with nicotine and menthol is inserted into the first compartment 110 and the second carrier material 106 impregnated with lactic acid is inserted into the second compartment 114.

The distal end cap 106 is then inserted into the proximal end of the body 104 such that the first air inlet 120 is aligned with the first compartment 110, the second air inlet 122 is aligned with the second compartment 114 and the third inlet 124 is aligned with the cavity 118.

The first compartment 110 and the second compartment 114 are substantially the same shape and size. The first compartment 110 and the second compartment 114 have a length of about 12 millimeters, a width of about 5 millimeters and a height of about 1.7 millimeters.

The first carrier material 112 and the second carrier material 116 comprise a non-woven sheet of PET/PBT and are substantially the same shape and size. The shape and size of the first carrier material 112 and the second carrier material 116 is similar to the shape and size of the first compartment 110 and the second compartment 114 of the cartridge 102, respectively.

The first air inlet 120 is in fluid communication with the first air outlet 126 so that a first air stream may pass into the cartridge 102 through the first air inlet 120, through the first compartment 110 and out of the cartridge 102 though the first air outlet 126. The second air inlet 122 is in fluid communication with the second air outlet 128 so that a second air stream may pass into the cartridge 102 through the second air inlet 122, through the second compartment 114 and out of the cartridge 102 though the second air outlet 128.

Prior to first use of the cartridge 102, the first air inlet 120 and the second air inlet 122 may be sealed by a removable peel-off foil seal or a pierceable foil seal (not shown) applied to the external face of the distal end cap 106. Similarly, prior to first use of the cartridge 102, the first air outlet 126 and the second air outlet 128 may be sealed by a removable peel-off foil seal or a pierceable foil seal (not shown) applied to the external face of the proximal end wall of the body 104.

Figures 1A, 1B, 1C, 1D, 1E, 1F, 1G:
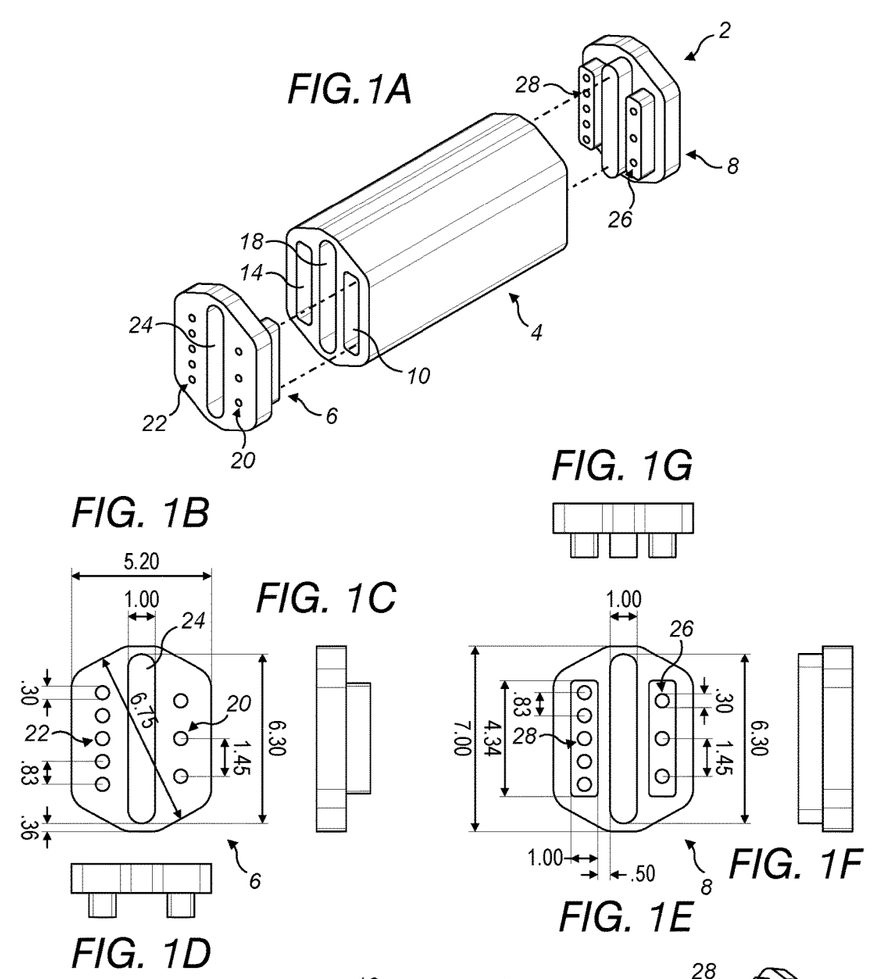
FIGS. 1A-1H show a cartridge according to a first embodiment of the invention.
Figure 1H:
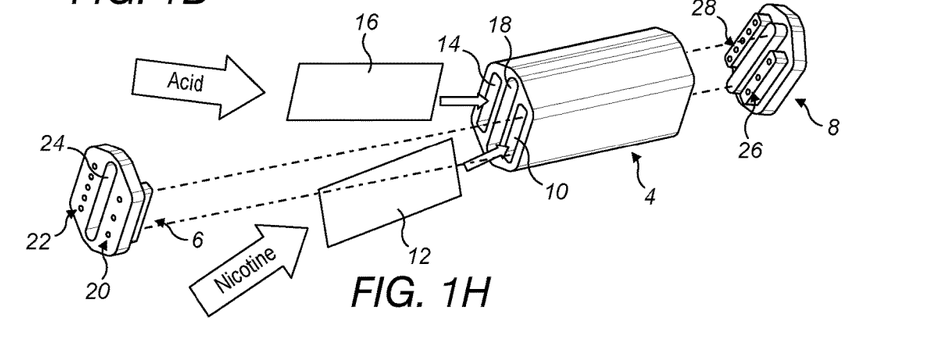
Figure 2A:
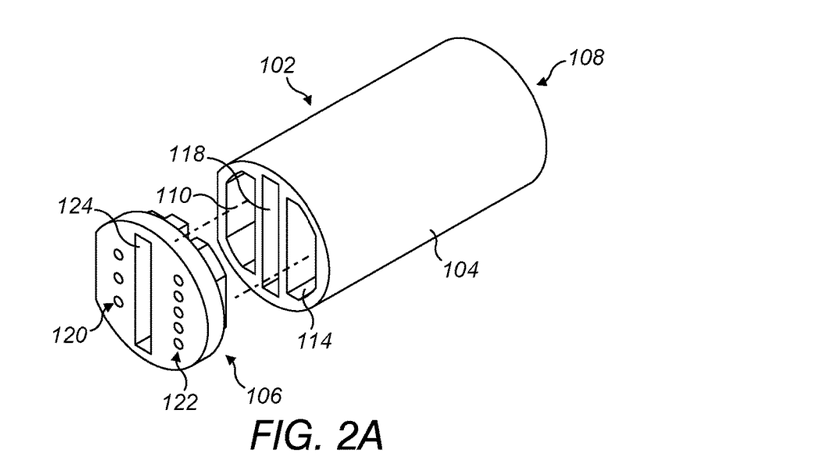
FIGS. 2A-2E show a cartridge according to a second embodiment of the invention.
Figure 2B:
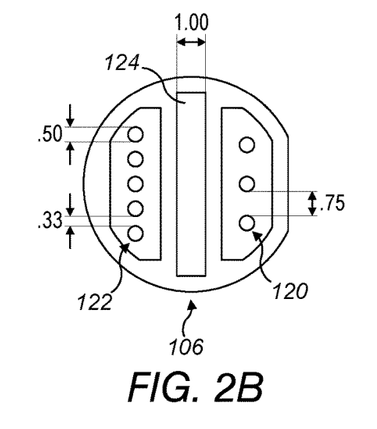
Figures 2C, 2D:
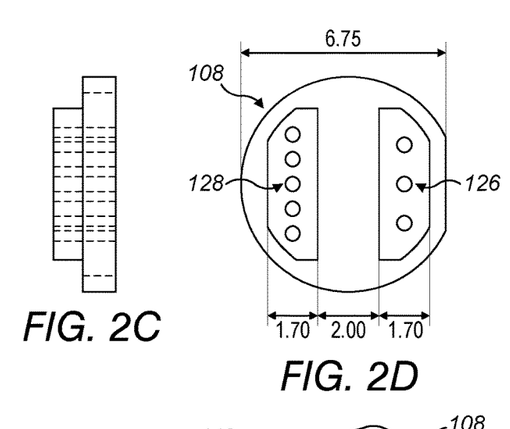
Figure 2E:
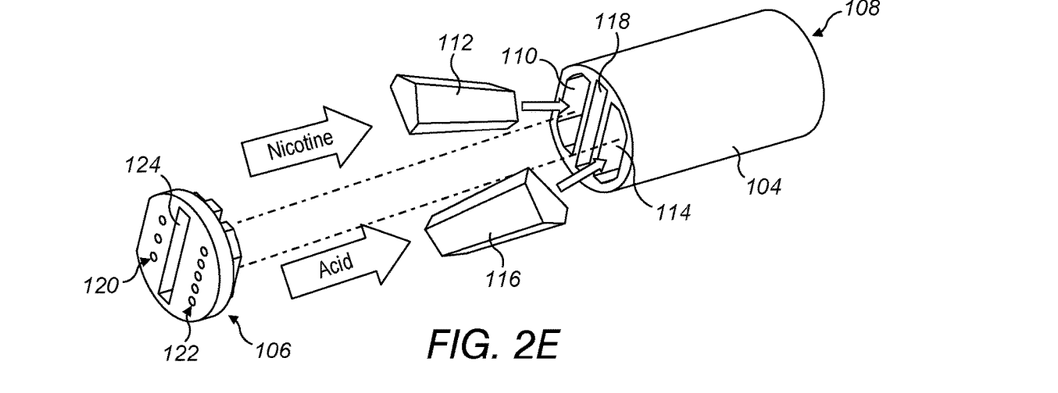
Figure 3:
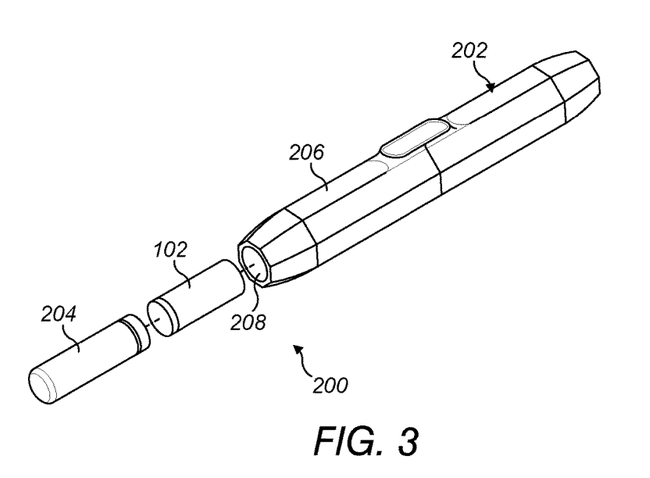
FIG. 3 shows an aerosol-generating system according to an embodiment of the invention.

FIG. 3 shows a schematic illustration of an aerosol-generating system 200 according to an embodiment of the invention for generating an aerosol comprising nicotine lactate salt particles.

The aerosol-generating system comprises an aerosol-generating device 202, a cartridge 102 according to the second embodiment of the invention shown in FIGS. 2A-2E and a mouthpiece 204.

The aerosol-generating device 202 comprises a housing 206 defining a cavity 208 for receiving the cartridge 102 and a heater (not shown) configured to heat both the first compartment 110 and the second compartment 114 of the cartridge 102.

The heater is a single elongate electric heater. The heater is positioned within the cavity 208 of the aerosol-generating device 202 and extends along the longitudinal axis of the cavity 208. The aerosol-generating device 202 further comprises a power supply and a controller (not shown) for controlling a supply of power from the power supply to the heater.

As the cartridge 102 is inserted into the cavity 208 of the aerosol-generating device 202, the heater passes through the third inlet 124 of the distal end cap 106 of the cartridge 102 and is received in the cavity 118 located between the first compartment 110 and the second compartment 114 of the cartridge 102. During use, the controller of the aerosol-generating device 202 controls the supply of power from the power supply aerosol-generating device 202 to the heater to heat the first compartment 110 and the second compartment 114 of the cartridge 102 to substantially the same temperature of about 100° C.

Once the cartridge 102 has been inserted into the cavity 208 of the aerosol-generating device 202, the distal end of the mouthpiece 204 is connected to the proximal end of the housing 206 of the aerosol-generating device 202.

In use, a user draws on the proximal end of the mouthpiece 204 to draw a first air stream through the first compartment 110 of the cartridge 102 and a second air stream through the second compartment 114 of the cartridge 102. As the first air stream is drawn through the first compartment 110 of the cartridge 102, nicotine vapour is released from the first carrier material 112 into the first air stream. As the second air stream is drawn through the second compartment 114 of the cartridge 102, lactic acid vapour is released from the second carrier material 116 into the second air stream.

The nicotine vapour in the first air stream and the lactic acid vapour in the second air stream react with one another in the gas phase in the mouthpiece 204 to form an aerosol of nicotine salt particles, which is delivered to the user through the proximal end of the mouthpiece 204.

In an alternative embodiment (not shown), the distal end of the mouthpiece 204 may be configured for engagement with the proximal end of the cartridge 102 rather than the proximal end of the housing 206 of the aerosol-generating device 202.

Figure 4:
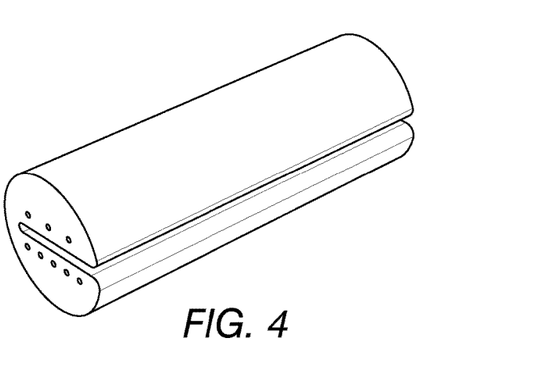
FIG. 4 shows a cartridge according to a third embodiment of the invention.

The cavity 118 of the cartridge 102 is enclosed along its length. As shown in FIG. 4, the cartridge may comprise a cavity for receiving a heater configured to heat the first compartment and the second compartment that is at least partially open along its length. This may advantageously facilitate insertion of the heater of the aerosol-generating device into the cavity of the cartridge.

Figures 5A, 5B, 5C:
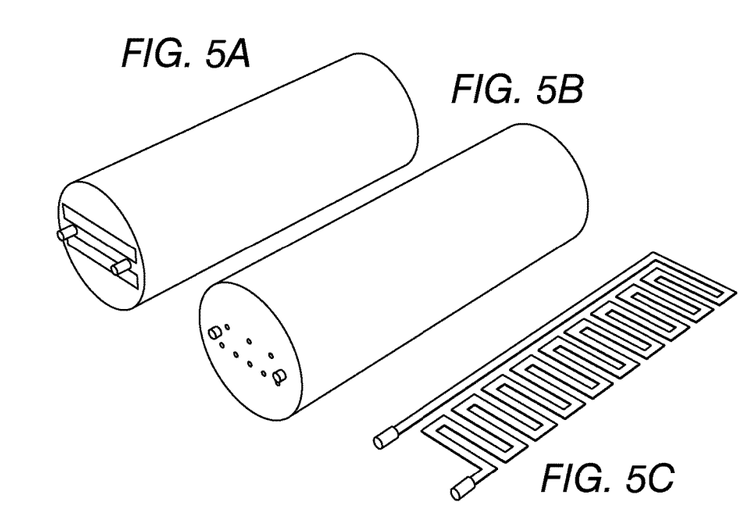
FIGS. 5A-5C show a cartridge according to a fourth embodiment of the invention.

As shown in FIGS. 5A-5C, rather than a cavity for receiving a heater configured to heat the first compartment and the second compartment, the cartridge may comprise a heater located between the first compartment and the second compartment. In such embodiments, the aerosol-generating device may be configured to supply power to the heater of the cartridge by means of one or more connection points of the heater at the distal end of the cartridge.

In the aerosol-generating system according to invention shown in FIG. 3, the aerosol-generating device 202 comprises an electric heater within the cavity 208 and the cartridge 102 comprises a cavity 118 for receiving the heater.

In an alternative embodiment (not shown), the aerosol-generating device 202 may comprise an inductive heater circumscribing the cavity 208 and the cartridge 102 may comprise a susceptor positioned within the cavity 118. In this alternative embodiment, during use the controller of the aerosol-generating device 202 controls the supply of power from the power supply of the aerosol-generating device 202 to the inductive heater to heat the susceptor within the cavity 118 of the cartridge 102. Once heated, the susceptor heats the first compartment 110 and the second compartment 114 of the cartridge 102.

The invention claimed is:

1. A cartridge for an aerosol-generating system, the cartridge comprising:
an elongate first compartment having a length $L_1$ and a maximum transverse cross-sectional area $A_1$, the first compartment having a first air inlet and a first air outlet and containing a nicotine source comprising a first carrier material loaded with from 1 milligram to 50 milligrams of nicotine; and
an elongate second compartment having a length $L_2$ and a maximum transverse cross-sectional area $A_2$, the second compartment having a second air inlet and a second air outlet and containing an acid source,
wherein the first compartment and the second compartment are arranged in parallel within the cartridge, and wherein a ratio $(L_1)^2:A_1$ is at least 12:1, and a ratio $(L_2)^2:A_2$ is at least 12:1.

2. The cartridge according to claim 1, wherein the ratio $(L_1)^2:A_1$ is between 12:1 and 400:1, and the ratio $(L_2)^2:A_2$ is between 12:1 and 400:1.

3. The cartridge according to claim 1, wherein the ratio $(L_1)^2:A_1$ is at least 15:1, and the ratio $(L_2)^2:A_2$ is at least 15:1.

4. The cartridge according to claim 3, wherein the ratio $(L_1)^2:A_1$ is between 20:1 and 100:1, and the ratio $(L_2)^2:A_2$ is between 20:1 and 100:1.

5. The cartridge according to claim 1, wherein the first compartment further comprises a flavourant.

6. The cartridge according to claim 1, further comprising a third compartment disposed in fluid communication with the first air outlet of the first compartment and the second air outlet of the second compartment.

7. The cartridge according to claim 1, wherein the acid source comprises a carboxylic acid.

8. The cartridge according to claim 7, wherein the acid source comprises a second carrier material impregnated with 2 milligrams to 60 milligrams of lactic acid.

9. The cartridge according to claim 1, wherein the first air inlet and the first air outlet of the first compartment, and the second air inlet and the second air outlet of the second compartment, are sealed by one or more removable or frangible barriers.

10. The cartridge according to claim 1, further comprising a cavity disposed between the first compartment and the second compartment, configured to receive a heater configured to heat the first compartment and the second compartment.

11. The cartridge according to claim 1, further comprising a heater disposed between the first compartment and the second compartment, wherein the heater is configured to heat the first compartment and the second compartment.

12. An aerosol-generating system, comprising:
a cartridge comprising:
an elongate first compartment having a length $L_1$ and a maximum transverse cross-sectional area $A_1$, the first compartment having a first air inlet and a first air outlet and containing a nicotine source comprising a first carrier material loaded with from 1 milligram to 50 milligrams of nicotine, and
an elongate second compartment having a length $L_2$ and a maximum transverse cross-sectional area $A_2$, the second compartment having a second air inlet and a second air outlet and containing an acid source,
wherein the first compartment and the second compartment are arranged in parallel within the cartridge, and
wherein a ratio $(L_1)^2:A_1$ is at least 12:1, and a ratio $(L_2)^2:A_2$ is at least 12:1; and
an aerosol-generating device comprising:
a housing defining a cavity configured to receive at least a portion of the cartridge, and
a heater configured to heat the first compartment and the second compartment of the cartridge.

13. The aerosol-generating system according to claim 12, wherein the heater is disposed within the cavity of the aerosol-generating device, and
wherein the cartridge further comprises another cavity disposed between the first compartment and the second compartment, being configured to receive the heater.

14. The aerosol-generating system according to claim 12, wherein the cartridge comprises a susceptor disposed between the first compartment and the second compartment, and the heater comprises an inductive heater surrounding at least a portion of the cavity of the aerosol-generating device.

15. An aerosol-generating system, comprising:
a cartridge comprising:
an elongate first compartment having a length Li and a maximum transverse cross-sectional area $A_1$, the first compartment having a first air inlet and a first air outlet and containing a nicotine source comprising a first carrier material loaded with from 1 milligram to 50 milligrams of nicotine,
an elongate second compartment having a length $(L_2)$ and a maximum transverse cross-sectional area $A_2$, the second compartment having a second air inlet and a second air outlet and containing an acid source, and
a heater disposed between the first compartment and the second compartment, configured to heat the first compartment and the second compartment,
wherein the first compartment and the second compartment are arranged in parallel within the cartridge, and
wherein a ratio $(L_1)^2:A_1$ is at least 12:1, and a ratio $(L_2)^2:A_2$ is at least 12:1; and
an aerosol-generating device comprising:
a housing defining a cavity configured to receive at least a portion of the cartridge, and
a power supply configured to supply power to the heater of the cartridge.

\* \* \* \* \*